United States Patent [19]

Ichikawa et al.

[11] Patent Number: 5,807,656
[45] Date of Patent: Sep. 15, 1998

[54] POLYHYDROXY COMPOUND AND A POSITIVE PHOTORESIST CONTAINING THE SAME

[75] Inventors: Koji Ichikawa; Haruyoshi Osaki; Yasunori Uetani, all of Osaka; Yoshiyuki Takata, Kobeshi, all of Japan

[73] Assignee: Sumitomo Chemical Company, Limited, Osaka, Japan

[21] Appl. No.: 709,323

[22] Filed: Sep. 4, 1996

Related U.S. Application Data

[63] Continuation of Ser. No. 476,570, Jun. 7, 1995, abandoned.

[30] Foreign Application Priority Data

Jun. 15, 1994 [JP] Japan .................................. 6-133096
Jul. 27, 1994 [JP] Japan .................................. 6-175687

[51] Int. Cl.$^6$ .................................................. G03F 7/023
[52] U.S. Cl. ........................ 430/191; 430/192; 430/193; 568/720
[58] Field of Search .................... 430/165, 191, 430/192, 193; 568/720

[56] References Cited

U.S. PATENT DOCUMENTS 5,059,507  10/1991  Uetani et al. ............................ 430/193
5,340,686  8/1994   Sakaguchi et al. ...................... 430/191
5,376,497  12/1994  Kawata et al. .......................... 430/191
5,407,779  4/1995   Uetani et al. ............................ 430/192
5,413,895  5/1995   Tomioka et al. ........................ 430/192

*Primary Examiner*—John S. Chu
*Attorney, Agent, or Firm*—Birch, Stewart, Kolasch & Birch, LLP

[57] ABSTRACT

A polyhydroxy compound represented by the following formula (I):

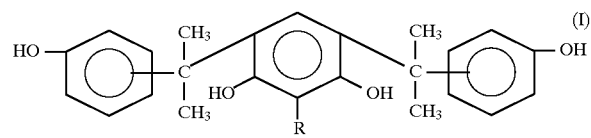

and a positive resist composition which comprises an alkali-soluble resin, a quinonediazide sulfonic acid ester, and a polyhydroxy compound of formula (I) or a polyhydroxy compound represented by the following formula (C):

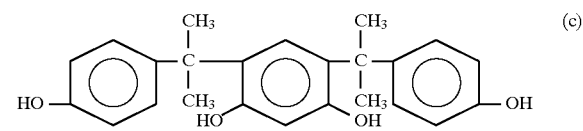

which is satisfactory in properties such as sensitivity, resolution, τ-value and peeling off resistance.

7 Claims, No Drawings

POLYHYDROXY COMPOUND AND A POSITIVE PHOTORESIST CONTAINING THE SAME

This application is a continuation of application Ser. No. 08/476,570 filed on Jun. 7, 1995, now abandoned.

BACKGROUND OF THE INVENTION

The present invention relates to a positive resist composition sensitive to radiation such as ultraviolet rays and far ultraviolet rays including excimer lazer.

The present invention also relates to a polyhydroxy compound which is usable as an ingredient of the positive resist composition.

A positive resist composition comprising an alkali-soluble resin;

a 1,2-quinonediazide compound;

and at least one compound selected from compounds represented by the following formula:

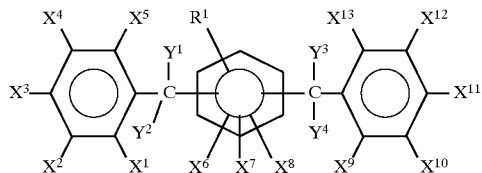

wherein $X^1$–$X^{13}$ each represent hydrogen, alkyl, alkoxy or hydroxy, provided that at least one of $X^1$–$X^5$, at least one of $X^6$–$X^8$ and at least one of $X^9$–$X^{13}$ are hydroxy;

$Y^1$–$Y^4$ each represent hydrogen or alkyl; and $R^1$ represents hydrogen or —COOR$^2$ wherein $R^2$ represents hydrogen, alkyl or aryl or $R^1$ is a residue represented by the following formula:

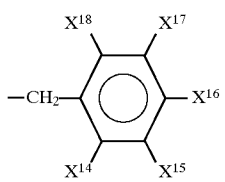

wherein $X^{14}$–$X^{18}$ each represent hydrogen, alkyl, alkoxy or hydroxy is described in JP-A-4-299348.

However, this composition is not satisfactory in properties such as sensitivity, resolution, τ-value and resistance against peeling off of the coated resist film caused by decomposition of sensitizer at its exposure to radiation (hereinafter referred to as "peeling off resistance"), and solubility in solvents used for making resist solution (hereinafter referred to as "sulubility un resist solvents").

The object of the present invention is to provide a novel polyhydroxy compound and a positive resist composition which is excellent in balance among its properties such as sensitivity, resolution, τ-value and peeling off resistance, and solubility in resist solvents.

SUMMARY OF THE INVENTION

The present invention provides a polyhydroxy compound represented by the following formula (I):

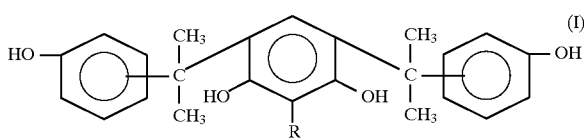

wherein R represents alkyl having six or less carbon atoms.

The present invention also provides a positive resist composition which comprises an alkali-soluble resin, a quinonediazide sulfonic acid ester, and a polyhydroxy compound represented by the following formula (c):

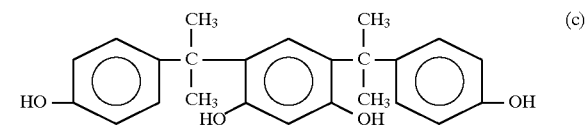

or a polyhydroxy compound of formula (I).

As preferred examples of polyhydroxy compounds of formula (I), a compound of the following formula (a) and a compound of the following formula (b) can be mentioned.

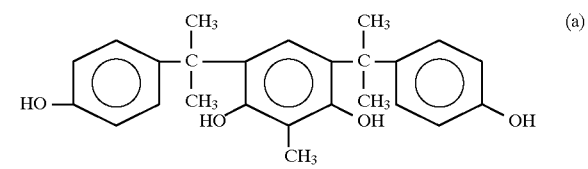

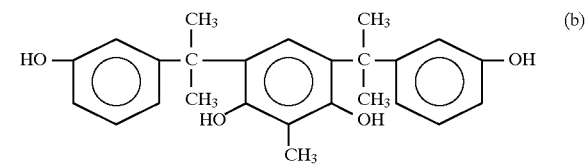

The polyhydroxy compounds of formula (I) can be produced, for example, by reacting isopropenylphenol and a 2-alkylresorcin in the presence of an acidic catalyst such as hydrochloric acid and in the presence of an organic solvent such as toluene. The amount of isopropenylphenol used in the reaction is preferably 2 moles or more per 1 mole of 2-alkylresorcin. The reaction temperature is preferably from room temperature to 70 ° C. The reaction time is usually from 1 to 10 hours.

The polyhydroxy compound of formula (c) is a known compound mentioned in JP-A-4-364147.

The quinonediazide sulfonic acid ester used in the present invention can be produced by conducting a condensation reaction of a phenol compound with a 1,2-benzoquinonediazide-4-sulfonic acid halide, 1,2-naphthoquinonediazide-4-sulfonic acid halide or 1,2-naphthoquinonediazide-5-sulfonic acid halide in the presence of an organic base such as triethylamine.

Examples of the phenol compound used for producing the quinonediazide sulfonic acid ester include hydroquinone; resorcin; phloroglucinone; alkyl gallate; a phenol compound represented by the following formula (II):

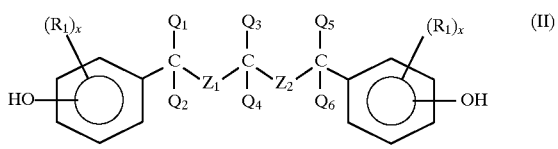

wherein $R_1$ represents hydrogen, halogen, unsubstituted or substituted alkyl, alkoxy or —OCOR$_3$ wherein $R_3$ represents unsubstituted or substituted alkyl or phenyl, $Q_1$–$Q_6$ each independently represent hydrogen, alkyl or phenyl, $Z_1$ and $Z_2$ each independently represent one of following divalent groups:

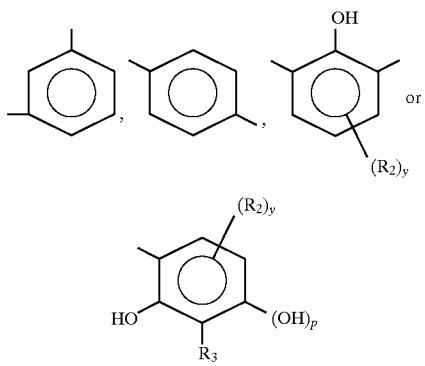

wherein $R_2$ represents hydrogen, halogen, unsubstituted or substituted alkyl, alkoxy or —$OCOR_3$ wherein $R_3$ is as defined above, y represents 1, 2 or 3 and p represents 0 or 1;

a phenol compound represented by the following formula (III):

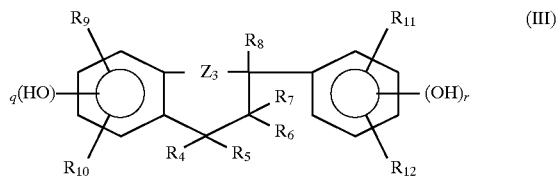

wherein $R_4$–$R_{12}$ each independently represent hydrogen, alkyl having 6 or less carbon atoms or cycloalkyl having 6 or less carbon atoms, $Z_3$ represents oxygen or a direct bond and q and r each independently represent 1, 2 or 3, provided that $R_4$ together with $R_5$, and $R_7$ together with $R_8$, may form a cyclopentyl ring or cyclohexyl ring in combination by linking their ends; and a hydroxybenzophenone represented by the following formula:

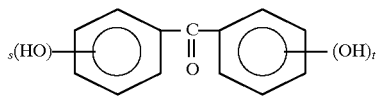

wherein s+t is an integer from 2 to 6.

As preferred examples of the phenol compounds mentioned above, a compound of formula (II) and a compound of formula (III) can be mentioned.

Preferred examples of alkyl denoted by $R_1$, $R_2$ or $R_3$ in formula (II) include straight chain or branched chain alkyl having 1–4 carbon atoms and methyl, ethyl and t-butyl are particularly preferred. Preferred examples of the substituent of substituted alkyl denoted by $R_1$, $R_2$ or $R_3$ in formula (II) include t-butyl, isopropyl and cycloalkyl having 5–8 carbon atoms.

Preferred examples of alkoxy denoted by $R_1$ or $R_2$ in formula (II) include straight chain or branched chain alkoxy having 1–4 carbon atoms. Preferred examples of alkyl denoted by $Q_1$–$Q_6$ in formula (II) include straight chain or branched chain alkyl having 1–4 carbon atoms. As particularly preferred examples of $Q_1$–$Q_6$ in formula (II), hydrogen and methyl can be mentioned.

Examples of the alkali soluble resin include polyvinylphenols and novolac resins. The novolac resin can be obtained by a condensation reaction of phenol compounds such as phenol, o-cresol, m-cresol, p-cresol, 2,5-xylenol, 3,5-xylenol, 3,4-xylenol, 2,3,5-trimethylphenol, 4-t-butylphenol, 2-t-butylphenol, 3-t-butylphenol, 3-ethylphenol, 2-ethylphenol, 4-ethylphenol, 2-t-butyl-5-methylphenol, 2-t-butyl-6-methylphenol, 2-t-butyl-4-methylphenol, 2-naphthol, 1,3-dihydroxynaphthalene, 1,7-dihydroxynaphthalene, 1,5-dihydroxynaphthalene or 3-methyl-6-cyclohexylphenol, singly or in combination of two or more, with aldehydes such as aliphatic aldehydes including formaldehyde, paraformaldehyde and glyoxal, and aromatic aldehyde including benzaldehyde, salicylaldehyde and terephthalaldehyde, singly or in combination of two or more, in the presence of a catalyst, according to a conventional method. The condensation reaction is usually carried out as a bulk reaction or in an appropriate solvent. The reaction temperature is usually 60°–120° C. and the reaction time is usually 2–30 hours. As examples of the catalyst, an organic acid such as oxalic acid, p-touenesulfonic acid, trichloroacetic acid and formic acid; an inorganic acid such as hydrochloric acid, sulfuric acid, perchloric acid and phosphoric acid; and a divalent metal salt such as zinc acetate and magnesium acetate can be mentioned.

Preferably, from the novolac resin thus obtained, a faction is recovered by a method such as fractionation or crystallization, in which the areal ratio of the GPC pattern, measured by using UV 254 nm detector, of the range in which the molecular weight as converted to polystyrene is not higher than 900 is 25% or less.

In the positive photoresist composition of the present invention, the amount of the quinonediazide sulfonic acid ester is usually 5–100 parts by weight per 100 parts by weight of the alkali soluble resin, and preferably the amount is 10–80 parts by weight, and the amount of polyhydroxy compound of formula (I) or formula (c) is usually 15–80 parts by weight per 100 parts by weight of the alkali soluble resin, and preferably the amount is 20–50 parts by weight.

A positive photoresist solution is prepared by mixing and dissolving the positive photoresist composition of the present invention in a resist solvent. As the resist solvent, solvents vaporizable at an appropriate rate and capable of giving a uniform and smooth coating film after evaporation are preferred. Examples of the solvents include ethylcellosolve acetate, methylcellosolve acetate, ethylcellosolve, methylcellosolve, propyleneglycol monomethyletheracetate, propyleneglycol monoethyletheracetate, ethylpyruvate, butyl acetate, methylisobutylketone, 2-heptanone, xylene, ethyl lactate and τ-butyrolactone. These solvents are used either independently or in the form of a mixture of two or more. The amount of the resist solvent is usually 40–90 parts by weight per 100 parts by weight of positive photoresist solution and preferably the amount is 55–85 parts by weight.

The balance among properties such as sensitivity, resolution and τ-value of a positive resist composition comprising a sensitizer and a binder resin can be improved by adding the polyhydroxy compound of formula (I) to the positive resist composition.

The positive resist composition of the present invention is excellent in properties such as sensitivity, resolution, τ-value and peeling off resistance, and solubility in resist solvents.

PREFERRED EMBODIMENT OF THE INVENTION

The present invention is explained in more detail with reference to the following examples. The invention is by no means limited by these examples. In the examples, parts means part by weight.

Example 1

Into a mixture of 31 g of 2-methylresorcin, 67 g of p-isopropenylphenol and 400 g of toluene, 0.3 g of 36% hydrochloric acid was added at a temperature of 40° C. After completion of the addition, the mixture was stirred for 3 hours at that temperature and then cooled and filtered to obtain a crystalline product. 70 g of ethylacetate and 10 g of water were added to dissolve the crystalline product and then the upper layer was separated and concentrated to evaporate off the ethylacetate. To the residue thus obtained, 400 g of toluene was added and recrystallization was carried out at room temperature while stirring. The precipitate produced by the recrystallization was filtered and dried to obtain 79 g of compound of formula (a).

MS: m/e=392 (M+)

$^1$HNMR (heavy dimethylsulfoxide, δppm) 1.58(s, 3H), 1.81(s, 3H), 6.62(d, 4H), 6.98(d, 4H), 6.98(s, 1H), 7.13(s, 2H), 9.02(s, 2H)

Example 2

Into a mixture of 31 g of 2-methylresorcin, 78.8 g of m-isopropenylphenol (purity 85%) and 400 g of toluene, 0.3 g of 36% hydrochloric acid was added at a temperature of 40° C. After completion of the addition, the mixture was stirred for 3 hours at that temperature and then cooled and filtered to obtain a crystalline product. 70 g of ethylacetate and 100 g of water were added to dissolve the crystalline product and then the upper layer was separated and concentrated to evaporate off the ethylacetate. To the residue thus obtained, 400 g of toluene was added and recrystallization was carried out at room temperature while stirring. The precipitate produced by the recrystallization was filtered and dried to obtain 75 g of compound of formula (b).

MS:m/e=392 (M+)

$^1$HNMR (heavy dimethylsulfoxide, δppm) 1.59(s, 2H), 1.82(s, 3H), 6.48(brd, J=5.6 Hz, 2H), 6.60(brd, 2H), 6.64(brd, J=7.9 Hz, 2H), 7.04(s, 1H), 7.00(dd, J=5.6, 7.9 Hz, 2H), 7.19(s, 2H), 9.05(s, 2H)

Synthesis Example 1

Into a mixture of 14 g of the following compound:

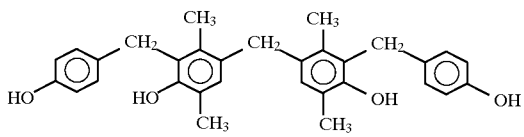

16.08 g of 1,2-naphthoquinonediazide-5-sulfonic acid chloride and 150 g of dioxane, 7.27 g of triethylamine was dropwise added at 20°–30° C. over 30 minutes and then the mixture was stirred at 30° C. for 6 hours. Thereafter, 2.44 g of acetic acid was added and then the mixture was stirred at that temperature for 1 hour. The reaction mixture thus obtained was filtered and washed with dioxane. The filtrate was added to a mixture of 5 g of acetic acid and 500 g of ion exchange water, and stirred for 1 hour. Thereafter, the precipitate was filtered and filtered cake was washed in ion exchange water by stirring. Then filtration was carried out and the filter cake was dried to obtain Sensitizer A.

Synthesis Example 2

Into a mixture of 6 g of the following compound:

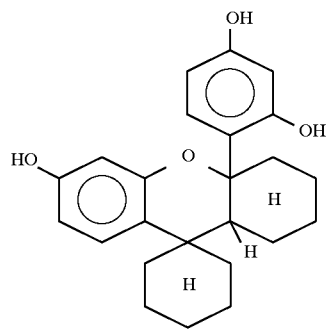

12.57 g of 1,2-naphthoquinonediazide-5-sulfonic acid chloride and 94 g of dioxane, 6.68 g of triethylamine was dropwise added at 20°–25° C. over 30 minutes and then the mixture was stirred at that temperature for 4 hour. The reaction mixture was added to ion exchange water, and then the precipitate was filtered. The filter cake was dried to obtain Sensitizer B.

Examples 3–4 and Comparative Examples 1–2

M-cresol, p-cresol, 2,5-xylenol, salicyl aldehyde and formaldehyde were allowed to react in a molar ratio of 3:2:5:1:7, respectively, to obtain a novolac resin having a weight average molecular weight of 8000 measured by GPC converted to polystyrene.

According to the formulation shown in the following Table, a polyhydroxy compound, a sensitizer and a novolac resin mentioned above were dissolved in a mixed solvent of 2-heptanone and τ-butyrolactone in which the weight ratio of 2-heptanone to τ-butyrolactone is 95:5. The amount of the solvent was adjusted so that a coated resist film having a thickness of 1.07 μm after baking is obtained.

The solution thus obtained was filtered through a filter having a pore size of 0.02 μ to prepare a resist solution. A silicon wafer washed in a conventional manner was coated with the resist solution by means of a spin coater and baked on a hot plate at 90° C. for one minute. Subsequently, the wafer was exposed to light by using a reduction projection exposing machine having an exposure wavelength of 365 nm (i-line) (NSR 2005i9C, NA=0.57, manufactured by Nikon Corp.) while stepwise changing the amount of exposure.

Subsequently, the wafer was baked on a hot plate at 110° C. for one minute. Then, it was developed for one minute with SOPD (alkaline developing solution; product of Sumitomo Chemical Co., Ltd.) to obtain a positive pattern.

Sensitivity is an exposure amount (=exposure time) at which the film thickness become zero on a graph which was obtained by plotting the exposure amount against the retained film thickness.

τ-value was expressed in term of tan θ. The θ is obtained by plotting a normalized film thickness (=the retained film thickness/the original film thickness) against a logarithm of the exposure amount and calculating the inclination of the plotted line.

Resolution was evaluated by measuring the dimension of the minimum line-and-space pattern which could be resolved without film thickness decrease at an exposure amount giving 1:1 line-and-space (effective sensitivity).

The results are shown in the following Table.

TABLE

|  | Example 3 | Example 4 | Comparative exampl 1 | Comparative exampl 2 |
|---|---|---|---|---|
| Polyhydroxy compound [amount, part] | Compound (a) [3.9] | Compound (c) [3.9] | Compound (d) *1 [3.9] | Compound (e) *2 [3.9] |
| Sensitizer [amount, part] | A [5] B [1] | A [5] B [1] | A [5] B [1] | A [5] B [1] |
| Amount of the Novolac resin, part | 10.43 | 10.43 | 10.43 | 10.43 |
| Sensitivity [msec.] | 167.9 | 158.2 | 141.7 | *4 |
| Resolution [μm] | 0.30 | 0.30 | *3 | *4 |
| γ value | 4.48 | 4.90 | *3 | *4 |
| Peeling off resistance | good | normal | normal | *4 |

*1, *2: Compound (d) and (e) are compounds mentioned below.

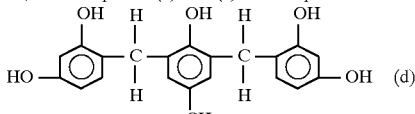
(d)

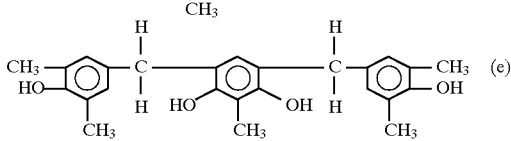
(e)

*3: unable to evaluate because of bad resist pattern shapes caused by necking.
*4: unable to evaluate because solubility of Compound (e) in the resist solution was so low that no resist solution could be prepared.

What we claim is:

1. A polyhydroxy compound represented by the following formula (I):

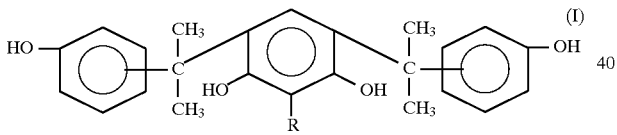
(I)

wherein R represent alkyl having 6 or less carbon atoms.

2. A polyhydroxy compound of claim 1 which is represented by the following formula (a) or (b):

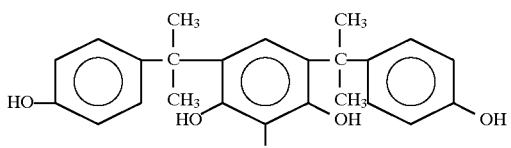
(a)

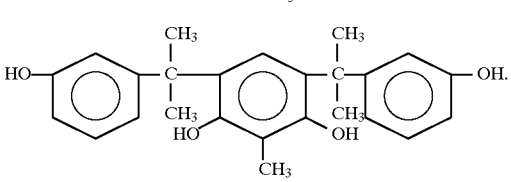
(b)

3. A positive resist composition which comprises an alkali-soluble resin, a quinonediazide sulfonic acid ester, and a polyhydroxy compound represented by the following formula (c):

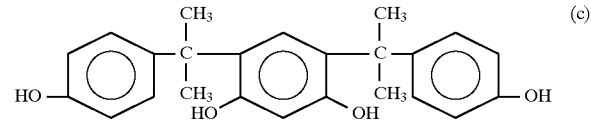
(c)

4. A positive resist composition which comprises an alkali-soluble resin, a quinonediazide sulfonic acid ester, and a polyhydroxy compound of claim 1.

5. A positive resist composition of claim 3 or 4, wherein the alkali-soluble resin is a novolac resin.

6. A positive resist composition of claim 3 or 4, wherein the quinonediazide sulfonic acid ester is a quinonediazide sulfonic acid ester of a phenol compound represented by the following formula (II):

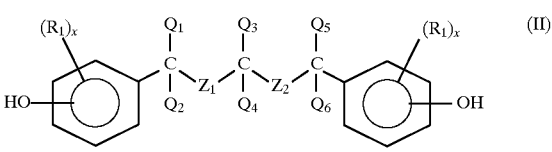
(II)

wherein $R_1$, represents hydrogen, halogen, unsubstituted alkyl, substituted alkyl, alkoxy or $-OCOR_3$ wherein $R_3$ represents unsubstituted alkyl, substituted alkyl or phenyl, $Q_1-Q_6$ each independently represent hydrogen, alkyl or phenyl, $Z_1$ and $Z_2$ each independently represent one of following divalent groups:

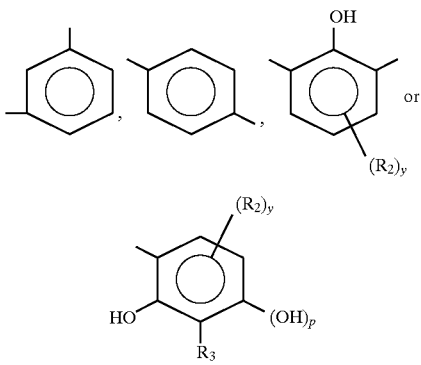

wherein $R_2$ represents hydrogen, halogen, unsubstituted alkyl, substituted alkyl, alkoxy or $-OCOR_3$ wherein $R_3$ is as defined above, y represents 1, 2 or 3 and p represents 0 or 1, and wherein substituents for the substituted alkyl are selected from the group consisting of t-butyl, isopropyl and cycloalkyl having 5–8 carbon atoms.

7. A positive resist composition of claim 3 or 4, wherein the quinonediazide sulfonic acid ester is a quinonediazide sulfonic acid ester of a phenol compound represented by the following formula (III):

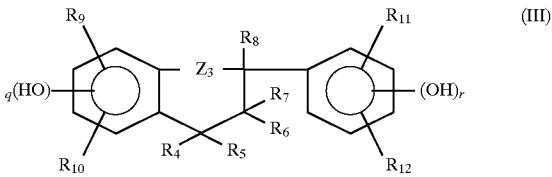
(III)

wherein $R_4$–$R_{12}$ each independently represent hydrogen, alkyl having 6 or less carbon atoms or cycloalkyl having 6 or less carbon atoms, $Z_3$ represents oxygen or a direct bond and q and r each independently represent 1, 2 or 3, provided that $R_4$ together with $R_5$, and $R_7$ together with $R_8$, may form a cyclopentyl ring or cyclohexyl ring in combination by linking their ends.

* * * * *